United States Patent [19]

Pawloski

[11] Patent Number: 4,824,872

[45] Date of Patent: Apr. 25, 1989

[54] NEOCARBYL-SUBSTITUTED PHOSPHORATES

[75] Inventor: Chester E. Pawloski, Bay City, Mich.

[73] Assignee: The Dow Chemical Company, Midland, Mich.

[21] Appl. No.: 125,911

[22] Filed: Nov. 27, 1987

Related U.S. Application Data

[62] Division of Ser. No. 843,452, Mar. 24, 1986, Pat. No. 4,739,091.

[51] Int. Cl.$^4$ ............................ C08J 9/00; C08K 9/00
[52] U.S. Cl. ...................................... 521/107; 521/85; 521/906
[58] Field of Search ......................... 521/85, 906, 107

[56] References Cited

U.S. PATENT DOCUMENTS

| | | | |
|---|---|---|---|
| 24,514 | 8/1958 | Hoppe et al. | 260/2.5 |
| 3,132,169 | 5/1964 | Birum et al. | 260/461 |
| 3,250,827 | 5/1966 | Schroll | 521/85 |
| 3,324,205 | 6/1967 | Carpenter et al. | 260/963 |
| 3,755,212 | 8/1973 | Dunlap et al. | 260/2.5 |
| 3,821,130 | 6/1974 | Barron et al. | 260/2.5 |
| 3,849,146 | 11/1974 | Walters et al. | 96/107 |
| 3,928,299 | 12/1975 | Rosenkranz et al. | 260/89.5 |
| 4,083,825 | 4/1978 | Albright et al. | 260/45.7 |
| 4,098,759 | 7/1978 | Noetzel et al. | 521/85 |
| 4,205,022 | 5/1980 | Nicholson et al. | 521/85 |
| 4,298,709 | 11/1981 | Ginter et al. | 521/169 |
| 4,576,971 | 3/1986 | Baumgartner et al. | 521/85 |
| 4,594,364 | 6/1986 | Pawloski et al. | 521/85 |

OTHER PUBLICATIONS

"Reactivite des Phosphoramidures: II., Preparation d'oxo-2 oxazaphosphorinanes-1,3,2" *Journal of Organometallic Chemistry*, 66 (1974) 71–79.

"Standard Test Method for Surface Burning Characteristics of Building Materials," ASTM Designation: E 84–84a, 315–332.

"A New High Efficiency Flame Retardant for Flexible Polyurethane Foam," Rose et al. paper presented at the 29th Annual Technical-Marketing Conference, sponsored by the Society of the Plastics Industry, at Reno, Nevada, Oct. 23–25, 1985.

"Standard Method for Measuring the Minimum Oxygen Concentration to Support Candle-Like Combustion of Plastics (oxygen index)," ASTM Designation: D 2863–2877, 635–641.

"Wrap-Up," section of Chemical Week, Oct. 30, 1985, 17.

"Flame Retardant Chemicals," product information of Great Lakes Chemical Corporation, dated Oct. 18, 1985.

"California Technical Bulletin 117: Requirements, Test Procedure and Apparatus for Testing the Flame Retardance of Resilient Filling Materials Used in Upholstered Furniture," State of California Department of Consumer Affairs, Bureau of Home Furnishings, North Highlands, California: Appendix D.

*Primary Examiner*—John Kight
*Assistant Examiner*—Dennis R. Daley
*Attorney, Agent, or Firm*—Christopher John Rudy

[57] ABSTRACT

Included is a process for the preparation of a ((neocarbyl)contrasting-halo-substituted)phosphorate comprising serially contacting (1) a phosphorus trihalide with a neocarbyl alcohol; (2) an oxirane; (3) a halogenating agent; and (4) an oxirane, under conditions sufficient to prepare the ((neocarbyl)contrasting-halo-substituted)-phosphorate. The phosphate can be very pure.

Also included is a method for improving a production characteristic of flame-retardant polyurethanes. The characteristic may be selected from the group consisting of (1) processability; (2) scorch; (3) odor; (4) flame-retardant efficiency; and (5) combinations thereof. The method comprises incorporation into a polyurethane an amount effective to reduce combustibility of the foregoing phosphorate flame retardant under conditions sufficient to improve said characteristic. Also included is the flame-retardant polyurethane composition of said method. Preferably, the polyurethane is a foam, especially a flexible foam and most especially flexible slabstock foam.

10 Claims, No Drawings

4,824,872

NEOCARBYL-SUBSTITUTED PHOSPHORATES

CROSS REFERENCE TO A RELATED APPLICATION

This is a divisional application of U.S. application Ser. No. 843,452, filed Mar. 24, 1986, now issued as U.S. Pat. No. 4,739,091.

FIELD

The invention concerns organic phosphorates. It also concerns their use, especially in flexible polyurethane foams.

BACKGROUND

Birum et al., U.S. Pat. No. 3,132,169 (1964) (incorporated herein by reference), disclose the preparation of certain ((neocarbyl-substituted) mixed bis(-halogenated))phosphorates. These phosphorates are useful flame retardants.

However, these phosphorates are typically mixtures wherein the bis(halogenated) moieties, in relation to the phosphorus, are, for example, not only (bromoalkyl)(-chloroalkyl) but also bis(bromoalkyl) and bis(chloroalkyl). See, e.g., Brault et al., *J. Organometallic Chem.*, 66, 71–79 (1974). Perhaps the presence of such a mixture of phosphorates is a reason Albright et al., U.S. Pat. No. 4,083,825 (1978), disclose that (3bromo-2,2-dimethylpropyl)(2-bromopropyl)(2-chloropropyl)phosphorate is not a substantially nonscorching flame retardant with a flexible polyurethane foam.

Thus, a problem in the art is the simple and efficient preparation of higher purity ((neocorbyl-substituted) mixed bis(halogenated))phosphorates. Another problem is the production of polyurethane foams which are more highly marketable, such as, for example, in slabstock flexible foams in which scorch, odor, flame retardant efficiency and processability are among production characteristics needing improvement.

SUMMARY

In one aspect, the invention is a process for the preparation of a ((neocarbyl)contrasting-halo-substituted)-phosphorate comprising serially contacting
(1) phosphorus trihalide with a neocarbyl alcohol;
(2) an oxirane;
(3) a halogenating agent; and
(4) an oxirane,
under conditions sufficient to prepare the ((neocarbyl)-contrasting-halo-substituted)phosphorate.

In another aspect, the invention is a method for improving a production characteristic of flame-retardant polyurethanes comprising incorporation into a polyurethane an amount effective to reduce combustibility of the ((neocarbyl)contrasting-halo-substituted)phosphorate flame-retardant compound under conditions sufficient to improve said characteristic.

A further aspect of the invention is the flame-retardant polyurethane composition such as can be produced by said method. Polyurethanes are polymeric resinous materials which find utility in coatings, as foamed materials which are used in structural applications such as in insulating foams in buildings (e.g., rigid foams) and in cushioning foams in upholstering (e.g., flexible foams).

The invention efficiently prepares the ((neocarbyl)-contrasting-halo-substituted)phosphorates. The simple preparation can result in a highly pure product.

The invention may significantly improve marketability of commercial flame-retardant polyurethanes. It substantially solves one or more of the production characteristics of flame-retardant polyurethanes, for example, scorch, odor and processability ease, especially in foams and most especially in flexible slabstock foams. In commercial production, reductions in such characteristics are not only desirable but may provide a basis for competitive commercial viability.

ILLUSTRATIVE EMBODIMENTS

The ((neocarbyl)contrasting-halo-substituted)phosphorate is a tris(organic)phosphorate. The three organic moieties are apportioned among one neocarbyl and two contrasting-halo-substituted moieties.

The organic moieties can be hydrocarbon or substituted hydrocarbon. The substituent moieties can include halo, cyano, ether, chalconoether (e.g., —S—), acyl and sulfoxy.

The neocarbyl moiety has a quaternary (i.e., 4°) carbon. The 4° carbon is connectable to the phosphorus through aliphatic carbon to carbon or ether linkages. The neocarbyl moiety is connected to the phosphorus through an oxygen such as in a phosphate ester.

The neocarbyl moiety is preferably a β-neocarbyl moiety. The β-neocarbyl moiety is a saturated carbon-containing moiety which has the 4° carbon bonded directly to a carbon which forms a bond connectable to the phosphorus through an oxygen such as in a phosphate ester. The β-neocarbyl moiety is alkyl or haloalkyl, most preferably haloalkyl.

The two contrasting-halo-substituted moieties each contain at least one halo moiety which contrasts with a halo moiety contained in the other. The two contrasting-halo-substituted moieties are distinguished from the neocarbyl moiety in that if the contrasting-halo-substituted moieties contain a 4° carbon, the 4° carbon is connectable to the phosphorus through at least one linkage other than aliphatic carbon to carbon and ether linkages.

The two contrasting-halo-substituted moieties are preferably contrasting-haloalkyl moieties, for example, bromoalkyl in contrast with chloroalkyl. The contrasting-haloalkyl moieties do not contain a 4° carbon. The contrasting-haloalkyl moieties are each connectable to the phosphorus through an oxygen such as in a phosphate ester.

Connectable herein means directly or indirectly bonded such as by covalent bonds. Connected herein means directly bonded.

The ((neocarbyl)contrasting-halo-substituted)phosphate is preferably a (β-neocarbyl)(chloroalkyl)(-bromoalkyl)phosphorate. The (β-neocarbyl((chloroalkyl)bromoalkyl)phosphorate is preferably a phosphate ester of the formula $$\mathrm{XH_2C-\underset{\underset{CH_2Y}{|}}{\overset{\overset{CH_2Y}{|}}{C}}-CH_2O-\underset{\underset{OR'Z'}{\diagdown}}{\overset{\overset{O}{\|}}{P}}\overset{ORZ}{\diagup}}$$

wherein
X is hydrogen, halo or $C_{1-5}$ alkyl;
Y is independently at each occurrence hydrogen or halo;
Z and Z' are contrasting halo;
R is a residue of the oxirane of step (2); and R' is a residue of the oxirane of step (4).

The halo moieties herein generally include iodo, bromo, chloro and fluoro, and preferably include bromo and chloro. The contrasting halo moieties can be, for example, bromo and chloro.

The halide moieties of the phosphorus trihalide can be of bromide, chloride and fluoride, and preferably are of bromide and chloride. More preferably, the phosphorus trihalide is phosphorus tribromide or phosphorus trichloride, most preferably, phosphorus trichloride.

The neocarbyl alcohol is a mono-hydroxylated organic compound with the neocarbyl moiety. The position of the hydroxyl group corresponds to the oxygen through which the neocarbyl moiety is connected to the phosphorus of the ((neocarbyl)contrasting-halo-substituted)phosphorate. Representative examples of neocarbyl alcohols include 2,2-dimethylpropanol; 3-chloro-2,2-dimethylpropanol; 3-bromo-2,2-dimethylpropanol; 3-fluoro-2,2-dimethylpropanol; 3-iodo-2,2-dimethylpropanol; 3-cyano-2,2-dimethylpropanol; 3-phenyl-2,2-dimethylpropanol; 3-(meta-bromophenyl)-2,2-dimethylpropanol; 3-methoxy-2,2-dimethylpropanol; 2,2-dimethyl-1-butanol; 2,2-bis(chloromethyl)propanol; 2,2-bis(bromomethyl)propanol; 2-chloromethyl-2-bromomethylpropanol; 3-chloro-2,2-bis(chloromethyl)propanol; 3-bromo-2,2-bis(bromomethyl)propanol; 3-chloro-2,2-bis(bromomethyl)propanol; and 1-(2-hydroxyethoxy)-2,2-dimethylpropane. Thus, the neocarbyl alcohols do not contain moieties (other than the hydroxyl moiety) which react with the phosphorus trihalide, such as amino and mercapto. The $C_{5-12}$ (i.e., from 5 to about 12 carbons) neocarbyl alcohols with carbon, hydrogen, oxygen or halogen are preferred.

In preparing the ((neocarbyl)contrasting-halo-substituted)phosphate, the neocarbyl alcohol is preferably added slowly to the phosphorus trihalide. Preferably, the temperature of this first step is cool. Preferred cool temperatures include temperatures from about 20° C. to the freezing point of the reactant mixture. Pressures are preferably ambient. Preferably, this step is carried out until hydrogen halide ceases to evolve. For example, the evolving hydrogen halide is typically HCl when employing $PCl_3$.

The oxiranes employed in preparing the ((neocarbyl)-contrasting-halo-substituted)phosphorates can generally be any organic oxirane (i.e., epoxides otherwise the hydrocarbons or the substituted hydrocarbons which do not contain moieties other than the epoxide moiety which reacts with the phosphorus-containing compound from the previous step). Examples of oxiranes include ethylene oxide; propylene oxide; epichlorohydrin; epibromohydrin; 3-cyano-1,2-propylene oxide; 1,2-butylene oxide; styrene oxide; allyl glycidyl ether; and tert-butyl glycidyl ether, which is a dealkylatable epoxide that can be subsequently dealkylated with phosphoric acid or an aryl sulfonic acid such as disclosed by Ginter et al., U.S. Pat. No. 4,298,709 (1981) (incorporated herein by reference), the dealkylation providing a free hydroxyl group on the ((neocarbyl)-contrasting-halo-substituted)phosphorate. The $C_{2-8}$ (i.e., from 2 to about 8 carbon) oxiranes with carbon, hydrogen, oxygen or halogen are preferred.

The halogenating agent is a chemical means for incorporating a halo moiety into the ((neocarbyl)contrasting-halo-sustituted)phosphorate generally other than by the phosphorus trihalide of the first step). Preferred are sources of chlorine and bromine, such as elemental chlorine and bromine, bromine chloride and organic halogenating agents such as N-bromosuccinimide. Most preferred are elemental chlorine and bromine, especially elemental bromine.

The halogenating agent is preferably added slowly to the reaction mixture. The temperatures are preferably those such as the cool temperatures of the first step. Preferably, the halogenating of the third step is carried out with about two atomic equivalents of halogenating agent per molar equivalent of phosphorate intermediate of step (2). For example, about one mole of elemental bromine is preferably employed in the halogenation of step (3). Preferably, the halogenating is carried out until general completion of the reaction such as, for example, indicated by the ceassation of the decolorization caused by the reaction of the added halogenating agent elemental bromine (i.e., the bromine color persists).

Preferably, the halogenating agent of step (3) is a contrasting halogenating agent, which incorporates a halo moiety which contrasts with a halo moiety which is a residue in the ((neocarbyl)contrasting-halo-substituted)phosphorate from the phosphorus trihalide. For example, a bromo moiety from elemental bromine employed in step (3) typically contrasts with a chloro moiety which is a residue in the ((neocarbyl)contrasting-halo-substituted)phosphorate from phosphorus trichloride.

Typically, the halogenation of the third step prepares a halogenated by-product which preferably corresponds to a residue of the oxirane from the second step. For example, 1-bromo-2-chloroethane can be prepared when the phosphorus trihalide is phosphorus trichloride and the oxirane of the second step is ethylene oxide, with the halogenating agent of the third step also typically providing a halo moiety (e.g., the 1-bromo moiety).

Halogenation additional to that of step (3) can be employed in appropriate circumstances. For example, ethylenically unsaturated bonds can typically be halogenated, by addition, with halogenating agents such as elemental chlorine and bromine and bromine chloride. The additional halogenation can be appropriately employed to incorporate contrasting-halo moieties.

The oxirane additions of the second step and of the fourth step are each typically exothermic and are usually carried out similarly. Preferably, the oxirane is slowly added to the reaction mixture. The temperatures are preferably from about 0° C. to about 80° C., most preferably about 20° C. to about 40° C. For the most part, pressures are preferably ambient atmospheric, although elevated pressures such as including pressures of about 50 psig (i.e., a gage pressure of about 345 kPa) can be advantageously employed with a gaseous oxirane such as ethylene oxide. Preferably, employment of an unsaturated oxirane such as allyl glycidyl ether is avoided in the oxirane addition of the second step (i.e., first oxirane addition).

Preferably, a Lewis acid catalyst such as aluminum tribromide, aluminum trichloride or titanium tetrachloride is employed in the oxirane additions. For the most part, amounts of the Lewis acid catalyst employed range from about 0.1 percent by weight to about 5 percent by weight, based on the amount of phosphorus intermediate from the preceeding step. Most preferably, about 0.5 percent by weight. The oxirane addition is preferably carried out until the reaction exotherm ceases.

The reaction can be run neat or can employ a diluent. Preferably, a liquid diluent is employed. Preferred liquid diluents include halogenated alkanes such as methylene chloride, chloroform, carbon tetrachloride and 1,2-dichloroethane.

The ((neocarbyl)contrasting-halo-substituted)phosphorate can be purified by known methods, such as in the Birum et al. patent (e.g., a neutral or basic water wash). A dilute acid wash of the mixed phosphate ester product can be employed with an aqueous mixture of the acid, especially with catalysts such as $AlCl_3$. The product mixture ratio is typically not changed by the dilute acid wash. Purification by distillation is a preferred step.

The process can prepare an extremely pure product which contains little or no phosphorate by-products such as corresponding bis(chloroalkyl) or bis(bromoalkyl)phosphorates, for example. Preferably, the ((neocarbyl)contrasting-halo-substituted)phosphorate is about 90 percent free of other bis(halo-substituted)phosphorate by-products, or more pure, as determined by gas chromatographic methods (e.g., capillary), more preferably about 95 percent or more pure, and most preferably, about 99 percernt or more pure.

The process thus can prepare a ((neocarbyl)contrasting-halo-substituted)phosphorate with an extremely low viscosity. Preferably, the viscosity of the phosphorate prepared by the instant process is lower than the viscosity of the corresponding phosphorate such as prepared by an alternate method such as by the method of the Birum et al. patent.

The following preferred general sequence further illustrates the preparation of the ((neocarbyl)contrasting-halo-substituted)phosphorates:

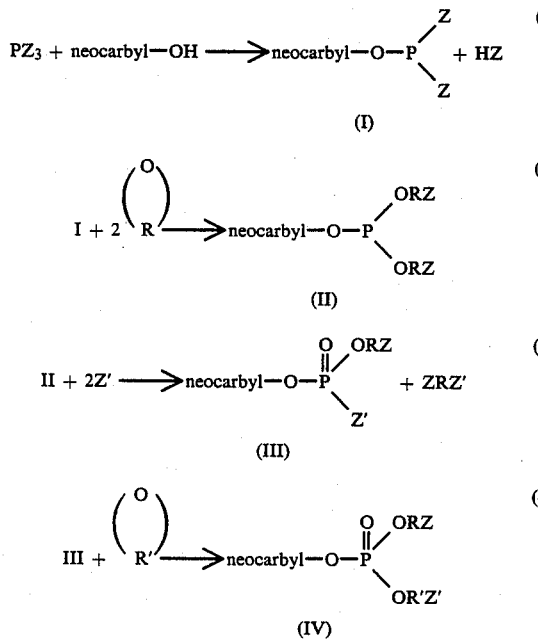

wherein R, R', Z and Z' are as defined herein, and conditions of each step are sufficient to prepare the illustrated compounds, for example, the phosphorus-containing compounds I, II, III and IV. If IV is aliphatically (i.e., ethylenically or acetylenically) unsaturated, the following additional halogenating step is preferably employed:

wherein Z'' is halo (e.g., F; Cl; Br; I, preferably Cl; Br), and at least one of Z' or Z'' connected to R or R' contrasts with Z (or Z'), and conditions are sufficient to prepare the illustrated compound ((IV)Z''$_2$).

The polyurethanes of this invention comprise organic polyisocyanates, polyahls and flame-retardant amounts of the phosphorate compounds of this invention. See, e.g., copending U.S. application Ser. No. 811,086, filed Dec. 19, 1985. See also, Rosenkranz et al., U.S. Pat. No. 3,928,299 (1975) (incorporated herein by reference). The polyurethanes can be prepared by known methods such as disclosed by Hoppe et al., U.S. Pat. No. Re 24,514 (reissued 1958) (incorporated herein by reference). The foams may also be prepared by the froth technique as described by Dunlap et al. in U.S. Pat. No. 3,755,212 (1973); by Barron et al. in U.S. Pat. No. 3,821,130 (1974); and by Walters et al. in U.S. Pat. No. 3,849,146 (1974) which are also incorporated herein by reference. The most preferred technique is the "one-shot" technique, where all the reactants are added simultaneously at the time of foaming, because it is generally used to prepare flexible polyurethane foams. Most, if not all, modern flexible slabstock (continuous) polyurethane foam machines are designed on the basis of this approach.

Of the polyahls, polyols are preferred. Especially preferred polyisocyanates include a mixture of 80 percent by weight 2,4-toluene diisocyanate with 20 percent by weight 2,6-toluene diisocyanate (commonly known as TDI 80/20 or T-80) and a mixture of 65 percent by weight 2,4-toluene diisocyanate with 35 percent 2,6-toluene diisocyaanate (i.e., TDI 65/35 or T-65). These are typically used in flexible polyurethane foams. The TDI 80/20 is more preferred.

The phosphorate flame-retardant compound is employed in an amount effective to produce said characteristics which are also flame-retardant in the polyurethane. This flame retardant is preferably employed in amounts of from about 5 pph to about 20 pph of the polyahl. By pph is meant parts by weight per hundred parts by weight of the polyahl (e.g., the polyol).

Preferred flexible polyurethane foam formulations with which the phosphorus compounds of the invention are incorporated include compositions such as follows:

| Reactant | Concentration (pph) |
|---|---|
| polyol | 100 |
| TDI index | 80–120 |
| flame-retardant | 6–18 |
| water | 1.0–5.5 |
| silicone surfactant | 0.2–3 |
| tertiary amine catalyst | 0.02–2 |
| auxiliary blowing agent | 0.5–40 |
| tin catalyst | 0.05–0.5 |

Also, foams with densities from about 1.0 pounds per cubic foot (i.e., about 16 kg per m$^3$) to about 4.0 pounds per cubic foot (i.e., about 64 kg per m$^3$) are preferred.

The polyurethane production characteristic(s) is (are) improved by the method of this invention, preferably selected from the group consisting of (1) processability;

(2) scorch;
(3) odor;
(4) flame-retardant efficiency; and
(5) combinations thereof.

Processability is a production characteristic which can be improved. A preferred measure of the processability is the Brookfield viscosity. The Brookfield viscosity is the viscosity measured at 25° C. on a Brookfield viscometer with a number 6 spindle rotating at 100 rotations per minute (i.e., rpm) submersed with sample in the center of a sample vessel with a width at least 125 percent of the spindle diameter.

Preferably, the Brookfield viscosity of the flame-retardant compound is 5000 centipoise (i.e., cP) or below at 25° C., more preferably 2500 cP or below and most preferably 500 cP or below. It is especially preferred that the Brookfield viscosity of the flame-retardant compound at 25° C. is 200 cP or below. The Brookfield viscosity can be as low as 50 cP or below.

Lower viscosity flame-retardant compounds may be obtained especially when R is $C_{2-3}$ alkyl, more especially ethylene. Also, lower viscosity flame-retardant compounds may be obtained when Y is independently each occurrence hydrogen or chloro, more especially when each Y is hydrogen.

Processability difficulties for higher viscosity flame-retardant compounds may be reduced by the use of diluents such as non-halogenated phosphate esters compounds. Preferably, such diluents are not used in processing.

Scorch is a production characteristic which may be improved by being reduced to minimal levels or even eliminated. A preferred measure of scorch is a $\Delta E$ in National Bureau of Standards (i.e., NBS) units by the Gardner Colorimeter test of about 10 or below, more preferably about 6 or below and most preferably about 4 or below. Determination of the $\Delta E$ value in NBS units by the Gardner Colorimeter test is more completely described in Albright et al., U.S. Pat. No. 4,083,825 (1978) from column 8, line 58 to column 11, line 23 (which material is incorporated herein by reference).

A more preferred measure of scorch is the Hunter Colorimeter test. The Hunter test differs from the Gardner test in that the color of both the sample set and control set are compared to the color of a standard pure white tile. The standard white tile may contain pure white MgO. If the sample versus control difference is determined by subtraction (i.e., sample-control) after this comparison to the title, the values of the Hunter test are typically substantially equivalent to values determined by the Gardner test.

The Gardner or Hunter Colorimeter test may be applied to any size sample prepared. Small-scale samples are a preferred size. Small-scale samples for polyurethane foams in this test are samples based on 100 g of polyol used in formulating the polyurethane foam and are poured directly upon creaming into a 7.5-inch (i.e., 19 cm) diameter, 6.0-inch (i.e., 15 cm) height clean paper cylinder (i.e., about one U.S. gallon in volume) at room temperature. A small-scale sample may be withdrawn from a larger sized production run or may be made in equivalent proportions thereto away from the larger sized production run. A more preferred size sample of polyurethane foam for the Gardner or Hunter Colorimeter test is a large-scale sample. Large-scale samples include foams made on continuous foam machines such as actually prepared in commercial production.

The most preferred polyurethane foam sample for the Gardner or Hunter Colorimeter test, especially with flexible foams, is a representative sample taken from a large-scale commercial production bun. The bun is cross-sectioned and the whole large-scale cross-section of bun is tested for scorch in the minimum number of required 4.0 square-inch (i.e., 26 cm$^2$) cross-sections (2.0 inches×2.0 inches, i.e., 5.1 cm×5.1 cm), and each smaller-scale $\Delta E$ value is summed, and the summation is divided by the required number of 4.0 square-inch cross-sections. This is the average $\Delta E$ value of the large-scale sample. The sample is 2.0 inches (i.e., 2.5 cm) in height. Thus, the sample is a cube of 2.0 inches per side.

Lower scorch-producing flame-retardant polyurethane compounds may be obtained especially when R and R' are ethylene. Also, lower scorch-producing flame-retardant polyurethane compounds may be obtained when X is bromo or hydrogen and Y is hydrogen or when X is chloro and Y is hydrogen.

As an indicia of scorch resistance when incorporated into a polyurethane, especially in a flexible foam, the thermal stability properties of the phosphorate flame-retardant compounds may be used. Preferably, the compositions have high thermal stability. One preferred method to measure this is by thermogravimetric analysis (i.e., TGA), where the sample tested is continuously monitored for weight loss as its temperature is progressively increased in an oven with a nitrogen atmosphere. Preferably, the progressive temperature increase is at a rate of 20° C. per minute from an initial temperature of 20° C. with the sample size initially between 0.010 g and 0.020 g. Under these preferred test conditions, thermogravimetric analyses preferably have a 50 percent weight loss of sample (i.e., TGA$_{50}$) at a temperature of about 200° C. or above, more preferably about 250° C. or above and most preferably about 280° C. or above. It is especially preferred that the TGA$_{50}$ is about 300° C. or above, more especially about 320° C. or above and most especially about 360° C. or above.

The thermogravimetric analysis at 10 percent weight loss (i.e., TGA$_{10}$) may be used also. The TGA$_{10}$ is otherwise measured as is the TGA$_{50}$. Preferred TGA$_{10}$ values include values found at about 160° C. or above, more preferably about 200° C. or above and most preferably about 240° C. or above.

Odor is a production characteristic which may be improved by being reduced or even eliminated. The presence of a halogenated neopentane, for example, tetrabromoneopentane, at levels of about 1-4 percent by weight, may cause the odor. Keeping the presence of such a halogenated neopentane to levels below 1 percent by weight, more preferably 0.5 percent by weight, typically eliminates such an odor in the resulting flame-retardant polyurethane, especially in slabstock foam. The instant process typically does not produce such an odoriferous halogenated neopentane.

Flame-retardant efficiency is a production characteristic which may be improved. By flame-retardant it is meant that the phosphorate, when incorporated into the polyurethane, reduces the propensity of the polyurethane to propagate combustion after the removal of a small-scale ignition source such as a lit Bunsen burner. The flame-retardant efficiency in additive-type flame-retardant phosphorus compounds incorporated with polyurethanes is typically a function of phosphorus-halogen content. Thus, brominated phosphorus ester compounds are preferred. A higher bromine content increases the flame-retardant efficiency by its mere presence within the composition.

One preferred method to measure this flame-retardant efficiency is an oxygen index (i.e., limiting oxygen index) measured by the oxygen demand test of ANSI/ASTM D-2863-77 (ASTM American National Standard) wherein the minimum concentration of oxygen in a mixture of dry $O_2$ and dry $N_2$ flowing upward, needed to cause combustion in a standard test column that will just support combustion under equilibrium conditions of candle-like burning is measured. Other conditions of the ANSI/ASTM D-2863-77 oxygen demand test include those set out in the ASTM American National Standard test (incorporated herein by reference).

Preferably, for ten appropriate A through D type (as in the D-3863-77 standard) specimens with the flame-retardant composition, the average limiting oxygen index (i.e., average LOI) is raised 10 percent or more, more preferably 20 percent or more and most preferably 30 percent or more, when measured either by time until extinguishing of the flame or distance of the burned specimen according to ASTM D-2863-77, when compared to ten otherwise comparable specimens without the flame-retardant composition. It is also preferred that the average LOI of ten appropriate A through D type specimens is raised to above 21, more preferably to about 25 or above and most preferably, to about 30 or above.

When incoporated into a rigid polyurethane foam, such as an insulating foam, preferred measures include the Steiner tunnel test of ASTM E-84 or the equivalent such as Underwriter's Laboratories 723. It is preferred that the rigid foam pass the E-84 test or equivalent with a Class III rating or better, more preferably a Class II rating or better. It may be desired to incorporate into the flame-retardant composition an amount effective to secure a Class I rating. Other tests such as the German DIN-4102-B2 test or its Swiss counterpart may be used.

When incorporated into a flexible polyurethane foam as a flame retardant, a preferred measure of the flame-retardant efficiency of the flame-retardant foam composition is the two-part California 117 test (i.e., both of the Vertical Burn tests and the Smoldering test) as in California Technical Bulletin 117, State of California Department of Consumer Affairs Bureau of Home Furnishings, North Highlands, Calif. (January, 1980) (which is incorporated herein by reference). It is preferred that the two-part California 117 test is passed by the flame-retardant flexible foam composition.

In each of the foregoing, it is preferred that the flame-retardant efficiency be substantially retained after aging. A preferred measure of this retention may be obtained by subjecting the flame-retardant polyurethane to elevated temperature (e.g., 104° C.) aging in a circulating air oven for 24 hours, followed by passing the requirements of the foregoing flame-retardant efficiency tests, such as in the case of a flexible foam by passing the California 117 Vertical Burn test.

Reduction of scorch and odor are each, and especially in combination, of high priority. Reduction of problems due to odor and processability or scorch and processability are also desirable. Reduction of each of the problems due to processability, scorch, odor and loss of flame-retardant efficiency is most desired.

Preferably, the method of employing the ((neocarbyl)contrasting-halo-substituted)phosphorate as a flame retardant is generally akin to the method disclosed in copending U.S. patent application Ser. No. 811,086, filed Dec. 19, 1985 (incorporated herein by reference).

SPECIFIC EMBODIMENTS

The following examples further illustrate the invention. Parts and percentages are by weight unless otherwise specified.

EXAMPLE 1

A. Preparation of 2,2-dimethylpropyl dichlorido phosphite

Into a flask is placed 207 g (1.5 mole) of $PCl_3$. It is stirred at about 0° C. to 10° C. while a solution of 88 g (1.0 mole) of neopentyl alcohol in 250 ml of methylene chloride is added dropwise. Upon completion of the addition, the reaction mixture is purged with nitrogen until HCl ceases to evolve. The product is then distilled to produce 167 g of an oil with a boiling point of 47° C.–48° C. at 2–3 mm Hg (i.e., about 266–399 Pa) at 88 percent theoretical yield.

B. Preparation of 2,2-dimethylpropyl(2-bromoethyl)(2-chloroethyl)phosphorate Into a flask are placed 63 g (0.33 mole) of the 2,2-dimethylpropyl dichlorido phosphite as from part A and 100 ml of methylene chloride. This mixture is stirred at 25° C. while a solution of 35 g (0.8 mole) of ethylene oxide in 50 ml of methylene chloride is added dropwise. Upon completion of this addition, the mixture is refluxed for one hour. Some of the low boilers are distilled off, and the mixture is cooled to 10° C. The, 52 g (0.33 mole) of bromine in 50 ml of methylene chloride is added dropwise. Upon completion of the reaction, the mixture is allowed to warm to room temperature. Then, 0.1 g of $AlCl_3$ is added, and a solution of 16 g (0.36 mole) of ethylene oxide in 25 ml of solvent is added dropwise. Upon completion of this reaction, some of the low boilers are distilled off, and the mixture is allowed to cool to 25° C. The reaction mixture is washed once with 50 ml of dilute HCl, once with 50 ml of dilute base, is dried over sodium sulfate and filtered. The solvent is distilled off under reduced pressure to produce an oil (108 g) with Brookfield viscosity (Number 6 spindle; 100 rpm; 25° C.) of 50 cP at 96 percent theoretical yield.

EXAMPLE 2

A. Preparation of 3-bromo-2,2-dimethyl dichlorido phosphite

By the method of Example 1, part A, 69 g (0.5 mole) of $PCl_3$ and 42 g (0.25 mole) of 3-bromo-2,2-dimethylpropanol in 100 ml of methylene chloride is contacted. An oil (47 g) with a boiling point of 74° C.–80° C. at 0.6 mm Hg (i.e., about 79.8 Pa) is obtained at 70 percent theoretical yield.

B. Preparation of 3-bromo-2,2-dimethylpropyl(2-bromoethyl)(2-chloroethyl)phosphorate Into a flask are placed 42 g (0.16 mole) of the 3-bromo-2,2-dimethylpropyl dichlorido phosphite as from part A and 100 ml of methylene chloride. This mixture is stirred while 15 g (0.34 mole) of ethylene oxide in 100 ml of methylene chloride is added dropwise. Upon completion of this addition, the mixture is refluxed for one hour, and some of the low boilers are distilled off. The mixture is allowed to cool to 10° C. Then it is stirred while 24 g (0.3 mole) of bromine are added dropwise. A slight color is present. The mixture is allowed to warm to room temperature, and 0.1 g of AlCl$_3$ is added. Then, 10 g (0.23 mole) of ethylene oxide in 50 ml of methylene chloride is added dropwise. Upon completion of this addition, the mixture is slowly heated to reflux. Some low boilers are distilled off, and the mixture is allowed to cool to room temperature. The mixture is washed twice with 50 ml portions of dilute aqueous HCl and once with 50 ml of dilute base water solution, separated, dried over sodium sulfate and filtered. The solvent is removed to produce 58 g (0.14 mole) of oil with Brookfield viscosity (Number 6 spindle; 100 rpm; 25° C.) of 75 cP at 89 percent theoretical yield. The $^{31}$P-nmr shows this to be the desired product. The overhead contains 2-bromo-1-chloroethane, but no neopentane dibromide is detected by nuclear magnetic resonance spectro (proton).

EXAMPLE 3

Preparation of 3-bromo-2,2-dimethylpropyl(2-bromopropyl)(2-chloroethyl)phosphorate In sequence, 89 g (0.33 mole) of 3-bromo-2,2-dimethylpropyl dichlorido phosphite as prepared by the general method of Example 2, part A, in 200 ml of methylene chloride, 35 g (0.80 mole) of ethylene oxide in 50 ml of methylene chloride, 48 g (0.6 mole) of bromine in 100 ml of methylene chloride, 0.1 g of AlCl$_3$, and 22 g (0.38 mole) of propylene oxide are contacted in the manner of Example 2, part B. An oil (140 g) with Brookfield viscosity (Number 6 spindle; 100 rpm; 25° C.) of 150 cP is obtained at 97 percent theoretical yield.

EXAMPLE 4

Preparation of 3-bromo-2,2-dimethylpropyl(2-bromoethyl)(2-chloropropyl)phosphorate In sequence, 89 g (0.33 mole) of 3-bromo-2,2-dimethylpropyl dichlorido phosphite as prepared by the general method of Example 2, part A, in 200 l of methylene chloride, 44 g (0.75 mole) of propylene oxide in 50 ml of methylene chloride, 48 g (0.6 mole) of bromine in 50 ml of methylene chloride, 0.1 g of AlCl$_3$, and 17 g (0.39 mole) of ethylene oxide in 50 ml of methylene chloride are contacted in the manner of Example 2, part B. An oil (144 g) with Brookfield viscosity (Number 6 spindle; 100 rpm; 25° C.) of 100 cP is obtained at 100 percent theoretical yield.

EXAMPLE 5

Preparation of 2,2-dimethylpropyl(2-chloro-3-(2,3-dibromopropoxy)-propyl)(2-chloroethyl)phosphorate Into a flask are placed 36 g (0.19 mole) of 2,2-dimethylpropyl dichlorido phosphite as prepared by Example 1, Part A, and 200 ml of methylene chloride. This is stirred at 25° C. while a solution of 18 g (0.41 mole) of ethylene oxide in 25 ml of methylene chloride is added dropwise. Upon completion of this addition, the mixture is cooled to 20° C. while 14 g (0.2 mole) of chlorine are bubbled into the reaction mixture. Upon completion of the reaction, 0.1 g of AlCl$_3$ is added, and 21.7 g (0.19 mole) of allyl glycidyl ether is added dropwise. Upon completion of this addition, the mixture is refluxed for one hour. Then, the mixture is cooled to 10° C., and then 30 g (0.19 mole) of bromine is added dropwise. Upon completion of the reaction, the mixture is washed once with 50 ml of dilute aqueous HCl (1N), 50 ml of dilute aqueous base (1 NaOH), dried over sodium sulfate and filtered. Low boilers are distilled off to produce an oil (95 g) with Brookfield viscosity (Number 6 spindle; 100 rpm; 25° C.) of 250 cP at 99 percent theoretical yield.

EXAMPLE 6

Laboratory studies of flame-retardant flexible foams including discoloration studies This example illustrates scorch characteristics of flame-retardant flexible polyurethane foams with a sample of a flame-retardant phosphorate (i.e., FR Sample) component.

| FR Sample | |
|---|---|
| (1) (Example 1) | |
| (2) (Example 2) | |
| (3) (Example 3) | |
| (4) (Example 4) | |
| (5) (Example 5) | |
| (A) DE-60-F (Comparative) | DE-60-F is a blend of pentabromodiphenyl oxide with a phosphate ester diluent available from Great Lakes Chemical |
| (B) THERMOLIN* 101 (Comparative) | Thermolin* 101 is tetrakis(2-chloroethyl) ethylene diphosphate and is available from the Olin Corporation |

From the following components, and the above-identified FR Samples, a 110 Index foam is prepared and is evaluated as follows.

| Components | Weight (g) |
|---|---|
| A-Side: | |
| Voranate* T-80 (80:20 molar ratio of toluene-2,4-diol-2,6-diisocyanates, respectively) | 62.3 |
| B-Side: | |
| 1. Voranol* 3137 (a polyol with a hydroxy number of about 53.4) | 100 |
| 2. FR Sample | 10 |
| 3. Water | 5 |
| 4. Q-25125 (silicone surfactant available from The Dow Corning Company) | 1 |
| 5. Methylene chloride | 6 |
| 6. NIAX TM A200 (amine catalyst available from Union Carbide) | 0.30 |
| 7. T-10 (50% solution of stannous octoate available from M & T Chemical) | 0.60 |

Foam preparation and Oven Aging Procedures

First, the A-side is weighed into a 4-ounce glass bottle and set aside. Second, the components of the B-side are weighed into a 32-ounce paper cup in the numerical order listed above. Third, the B-side is then mixed for 15 seconds on a variable speed overhead mixer. Fourth, the A-side is immediately added to the B-side and mixed for an additional 5 seconds. Fifth, the A-side/B-side mixture is poured into a one-gallon paper container.

Once four consecutive foams are prepared by this procedure, all four foam samples are placed in a preheated air circulating oven for 30 minutes. The foam samples are then removed from the oven and allowed to cool to room temperature for the following evaluation.

Cutting and Color Measurement Procedure

A two-inch cross-sectional slice is cut off the top of each foam sample. A two-inch section is then cut from the middle of each cross-sectional slice. The underside of this section is used for color determination.

Color is measured on a Macbeth Colorimeter meter using the Hunter Color Scale. The Hunter Color Scale compares the color of the sample to a standard white tile.

Three measurements are made for each sample and then averaged. The average delta E value ($\Delta E$) for each sample is then compared to the average $\Delta E$ value determined by the Hunter Color Scale for a foam containing no flame retardant. A value [$\Delta E$(FOAM)] is calculated according to the following equation.

$$\Delta E(FOAM) = \Delta E(SAMPLE) - \Delta E(NO\ FR\ FOAM)$$

The $\Delta E$(FOAM) values as are obtained of 70° C., 140° C. and 160° C. with FR Samples (1)–(5) are comparable to those values as are obtained with FR Samples (A) and (B). FR Samples (A) and (B) are typically sold as substantially nonscorching flame retardants. Thus, FR Samples (1)–(5) are substantially nonscorching flame retardants. The foams are flame-retardant. The foams with FR Samples (1)–(5) pass the requirements of the California 117 test.

EXAMPLE 7

Commercial-type production

If, by the one-shot technique, a commercial-type scale slabstock flexible polyurethane foam with about 110 index is prepared with about 1 pph of the phosphorate as prepared by the method of Examples 1–5 incorporated therein, the foam is easily processable and is flame-retardant. In addition, the foams exhibit high flame-retardant efficiency, passing the California 117 test as set out by the California 117 test requirements, are substantially nonscorching and are essentially non-odoriferous.

What is claimed is:

1. A method for improving a production characteristic selected from the group consisting of processability, scorch, odor, flame-retardant efficiency, and combinations thereof flame-retardant polyurethanes comprising incorporation of an amount of a flame-retardant compound of the general formula:

$$XH_2C-\underset{\underset{CH_2Y}{|}}{\overset{\overset{CH_2Y}{|}}{C}}-CH_2O-\overset{\overset{O}{\|}}{P}\diagup\overset{ORCl}{\underset{ORBr}{}}$$

wherein
X is selected from the group consisting of H, Cl, Br, and $C_{1-5}$ alkyl;

Y is independently at each occurrence selected from the group consisting of H, Cl and Br, and at least one X or Y is Cl or Br; and
R is independently at each occurence $C_{3-8}$ haloalkyl or $C_{6-8}$ haloalkoxyhaloalkyl, wherein the halo moieties are Cl or Br, or a saturated hydrocarbyl of the formula $C_nH_{2n}$ wherein n is an integer from 2 to about 8,
into a polyurethane foam under conditions sufficient to improve said characteristics.

2. The method of claim 1 wherein the flame-retardant polyurethane foam is a slabstock flexible polyurethane foam.

3. The method of claim 2 wherein said flame-retardant compound is 95 percent or more pure.

4. The method of claim 3 wherein said characteristic is scorch, and the foam is characterized as being substantially nonscorching.

5. The method of claim 4 wherein the foam is prepared by the one-shot process.

6. The method of claim 5 wherein said characteristic is odor, and the foam is characterized as being substantially non-odoriferous.

7. The method of claim 6 wherein said characteristic is flame-retardant efficiency, and the foam is characterized as passing the California 117 tests.

8. The method of claim 7 wherein X is Br; Y is H; R is selected from the group consisting of $C_2H_4$ and $C_3H_6$; and the foam is characterized as being substantially nonscorching with a $\Delta E$ of 4 or below based on the Hunter scale.

9. A flame-retardant polyurethane foam composition comprising a polyurethane foam having incorporated therein a flame retardant compound of the general formula:

$$XH_2C-\underset{\underset{CH_2Y}{|}}{\overset{\overset{CH_2Y}{|}}{C}}-CH_2O-\overset{\overset{O}{\|}}{P}\diagup\overset{ORCl}{\underset{ORBr}{}}$$

wherein
X is selected from the group consisting of H, Cl, Br, and $C_{1-5}$ alkyl;
Y is independently each occurrence selected from the group consisting of H, Cl and Br, and at least one X or Y is Cl or Br;
R is independently at each occurrence $C_{3-8}$ haloalkyl or $C_{6-8}$ haloalkoxyhaloalkyl, wherein the halo moieties are Cl or Br, or a saturated hydrocarbyl of the formula $C_nH_{2n}$ wherein n is an integer from 2 to about 8, and wherein the flame-retardant compound is at least 95 percent pure,
in an amount sufficient to reduce combustibility.

10. The composition of claim 9 wherein X is Br; Y is H; R is selected from the group consisting of $C_2H_4$ and $C_3H_6$; and the scorch is characterized by a substantially nonscorching polyurethane with a $\Delta E$ of 4 or below based on the Hunter scale, and wherein the composition is substantially non-odoriferous, and wherein flame-retardant efficiency is characterized by the composition's ability to pass the California 117 test.

* * * * *

UNITED STATES PATENT AND TRADEMARK OFFICE
CERTIFICATE OF CORRECTION

Page 1 of 2

PATENT NO. : 4,824,872

DATED : April 25, 1989

INVENTOR(S) : Chester E. Pawloski

It is certified that error appears in the above-identified patent and that said Letters Patent is hereby corrected as shown below:

Column 1, line 34 please delete "((neocorbyl-substituted) mixed bis(halogenated))phosphorates" and insert -- ((neocarbyl-substituted) mixed bis(halogenated))phosphorates --.

Column 3, lines 34-35 please delete "((neocarbyl)contrasting-halo-substituted)phosphate" and insert -- ((neocarbyl)contrasting-halo-substituted)phosphorate --.

Column 4, line 14 please delete "ceassation" and insert -- cessation --.

Column 5, line 23 please delete "percernt" and insert -- percent --.

Column 9, line 30 please delete "incoporated" and insert -- incorporated --.

Column 10, line 32 please delete "The," and insert -- Then, --.

Column 11, line 16 please delete "shows" and insert -- spectra shows --.

Column 11, line 43 please delete "200 1" and insert -- 200 ml --.

Column 13, line 40 please delete "1 pph" and insert -- 10 pph --.

UNITED STATES PATENT AND TRADEMARK OFFICE
CERTIFICATE OF CORRECTION

PATENT NO. : 4,824,872

DATED : April 25, 1989

INVENTOR(S) : Chester E. Pawloski

It is certified that error appears in the above-identified patent and that said Letters Patent is hereby corrected as shown below:

Column 14, line 10 please delete "characteristics" and insert --characteristic--.

Signed and Sealed this

Seventh Day of May, 1991

Attest:

HARRY F. MANBECK, JR.

Attesting Officer

Commissioner of Patents and Trademarks